(12) United States Patent
Takagi et al.

(10) Patent No.: US 6,946,268 B2
(45) Date of Patent: Sep. 20, 2005

(54) L-CYSTEINE PRODUCING BACTERIUM AND METHOD FOR PRODUCING L-CYSTEINE

(75) Inventors: Hiroshi Takagi, Fukui (JP); Masaru Wada, Fukui (JP); Shigeru Nakamori, Fukui (JP)

(73) Assignee: Ajinomoto Co., Inc., Tokyo (JP)

( * ) Notice: Subject to any disclaimer, the term of this patent is extended or adjusted under 35 U.S.C. 154(b) by 139 days.

(21) Appl. No.: 10/254,763

(22) Filed: Sep. 26, 2002

(65) Prior Publication Data

US 2003/0186393 A1 Oct. 2, 2003

(30) Foreign Application Priority Data

Sep. 28, 2001 (JP) ........................................ 2001-302008

(51) Int. Cl.[7] ............................ C12P 13/12; C12N 9/10; C12N 1/20; C12N 15/00; C07H 21/04
(52) U.S. Cl. ........................ 435/113; 435/193; 435/232; 435/252.33; 435/320.1; 536/23.2
(58) Field of Search ................................. 435/113, 193, 435/232, 252.33, 320.1; 536/23.2

(56) References Cited

U.S. PATENT DOCUMENTS

| 5,972,663 A | 10/1999 | Winterhalter et al. |
| 6,218,168 B1 | 4/2001 | Leinfelder et al. |

FOREIGN PATENT DOCUMENTS

| JP | 11-56381 | 3/1999 |
| JP | 11-155571 | 6/1999 |
| JP | 2000-504926 | 4/2000 |

OTHER PUBLICATIONS

H. Takagi, et al., FEMS Microbiology Letters, vol. 179, pp. 453–459, "Overproduction of L–Cysteine and L–Cystine by Expression of Genes for Feedback Inhibition–Insensitive Serine Acetyltransferase from Arabidopsis Thaliana in *Escherichia Coli*", 1999.

C. M. Dwivedi, et al., Biochemistry, vol. 21, no. 13, pp. 3064–3069, "Cloning, Purification, and Characterization of β–Cystathionase from *Escherichia Coli*", 1982.

W. Austin Newton, et al., The Journal of Biological Chemistry, vol. 240, no. 3, pp. 1211–1218, "Properties of Crystalline Tryptophanase", Mar. 1965.

E. Zdych, et al., Journal of Bacteriology, vol. 177, No. 17, pp. 5035–5039, XP–002239014, "Maly of *Escherichia Coli* is an Enzyme with the Activity of a βC–S L YASE (CYSTATHIONASE)", Sep. 1995.

C. Richaud, et al., The Journal of Biological Chemistry, vol. 268, No. 36, pp. 26827–26835, XP–002239015, "Directed Evolution of Biosynthetic Pathways", 1993.

E. A. Brown, et al., Journal of General Microbiology. vol. 136, pp.1017–1023, XP–008016322, "A Relationship Between L–Serine Degradation and Methionine Biosynthesis in *Escherichia Coli* K12", Jun. 1990.

V. Stewart, et al., Journal of Bacteriology. vol. 164. No. 2, pp. 731–740. XP–008016309, "Evidence for Transcription Antitermination Control of Tryptophanase Operon Expression in *Escherichia Coli* K12", Nov. 1985.

S. Nakamori, et al., Applied and Environmental Microbiology, vol. 64, No. 5, pp. 1607–1611, XP–002115630, "Overproduction of L–Cysteine and L–Cystine By *Escherichia Coli* Strains with a Genetically Altered Serine Acetyltransferase", May 1998.

F. C. Neidhardt, et al., ASM Press, pp. 386–387, XP–002239016, "*Escherichia Coli* and Salmonella, Cellular and Molecular Biology", 1996.

T. Clausen, et al., Journal of Molecular Biology, vol. 262, No. 2, pp. 202–224, XP–001005219, "Crystal Structure of the Pyridoxal–5'–Phosphate Dependent Cystathionine β–Lyase from *Escherichia Coli* at 1.83 A", 1996.

*Primary Examiner*—Manjunath N. Rao
*Assistant Examiner*—Christian L. Fronda
(74) *Attorney, Agent, or Firm*—Oblon, Spivak, McClelland, Maier & Neustadt, P.C.

(57) ABSTRACT

L-Cysteine is produced by culturing a bacterium belonging to the genus *Escherichia* having an L-cysteine producing ability and modified so that cystathionine-β-lyase activity or cystathionine-β-lyase activity and tryptophanase activity should be reduced or eliminated in a medium to produce and accumulate L-cysteine in the medium and collecting the L-cysteine from the medium.

18 Claims, 4 Drawing Sheets

SEQUENCE LISTING

<160> NUMBER OF SEQ ID NOS: 14

<210> SEQ ID NO 1
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

Met Glu Asn Phe Lys His Leu Pro Trp Met Phe Arg Ile Arg Val
1               5                   10                  15

<210> SEQ ID NO 2
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
cgcggatcca agccgcattc tgactg                                      26

```
<210> SEQ ID NO 3
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
cccaagcttc tgactcgggc taacgca                                27

<210> SEQ ID NO 4
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
cccaagcttg ccggtttcac tggcaa                                 26

<210> SEQ ID NO 5
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
ctatggatcc ttatagccac tctgtag                                27

<210> SEQ ID NO 6
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
cgcggatcca acagagcttc tgcgatacc                              29

<210> SEQ ID NO 7
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cggggtacca ctagcatgaa tattcgcgg                              29

<210> SEQ ID NO 8
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
cggggtacct accgcctata taaccagcc                              29

<210> SEQ ID NO 9
<211> LENGTH: 19
<212> TYPE: DNA
<213> ORGANISM: ARTIFICIAL SEQUENCE
<220> FEATURE:
<223> OTHER INFORMATION: SYNTHETIC DNA
```

<400> SEQUENCE: 9
aatatgagga tccgccagc                                                  19

<210> SEQ ID NO 10
<211> LENGTH: 1880
<212> TYPE: DNA
<213> ORGANISM: Escherichia coli

<400> SEQUENCE: 10

| | | | | | |
|---|---|---|---|---|---|
| aagcttttgc | taccaaaatc | agcggcgata | tcgttggcct | ggtttaagga | acgcgcttca    60 |
| gccagcagtt | gctgctcgcg | cttaagggac | gcttctgatt | gaagaactct | acgctcttac   120 |
| tgaagaagat | tgcccaggtg | actacggagg | ccaaaataag | cccaatcatc | acgcacttaa   180 |
| cgacaatatc | ggcgtgctga | tacataccccc | agacggaaag | gtccgtctgc | attaaattat   240 |
| tacccactgt | gtatctccag | gacgcaagtc | acaaaatctg | cgcataataa | tatcaaaacg   300 |
| acgtcgaatt | gatagtcgtt | ctcattacta | tttgcatact | gccgtacctt | tgctttcttt   360 |
| tccttgcgtt | tacgcagtaa | aaagtcacc | agcacgccat | ttgcgaaaat | tttctgcttt   420 |
| atgccaattc | ttcaggatgc | gcccgcgaat | attcatgcta | gtttagacat | ccagacgtat   480 |
| aaaaacagga | tcccgacat | ggcggacaaa | aagcttgata | ctcaactggt | gaatgcagga   540 |
| cgcagcaaaa | aatacactct | cggcgcggta | aatagcgtga | ttcagcgcgc | ttcttcgctg   600 |
| gtctttgaca | gtgtagaagc | caaaaaacac | gcgacacgta | atcgcgccaa | tggagagttg   660 |
| ttctatggac | ggcgcggaac | gttaacccat | ttctccttac | aacaagcgat | gtgtgaactg   720 |
| gaaggtggcg | caggctgcgt | gctatttccc | tgcggggcgg | cagcggttgc | taattccatt   780 |
| cttgctttta | tcgaacaggg | cgatcatgtg | ttgatgacca | acaccgccta | tgaaccgagt   840 |
| caggatttct | gtagcaaaat | cctcagcaaa | ctgggcgtaa | cgacatcatg | gtttgatccg   900 |
| ctgattggtg | ccgatatcgt | taagcatctg | cagccaaaca | ctaaaatcgt | gtttctggaa   960 |
| tcgccaggct | ccatcaccat | ggaagtccac | gacgttccgg | cgattgttgc | cgccgtacgc  1020 |
| agtgtggtgc | cggatgccat | cattatgatc | gacaacacct | gggcagccgg | tgtgctgttt  1080 |
| aaggcgctgg | atttttggcat | cgatgtttct | attcaagccg | ccaccaaata | tctggttggg  1140 |
| cattcagatg | cgatgattgg | cactgccgtg | tgcaatgccc | gttgctggga | gcagctacgg  1200 |
| gaaaatgcct | atctgatggg | ccagatggtc | gatgccgata | ccgcctatat | aaccagccgt  1260 |
| ggcctgcgca | cattaggtgt | gcgtttgcgt | caacatcatg | aaagcagtct | gaaagtggct  1320 |
| gaatggctgg | cagaacatcc | gcaagttgcg | cgagttaacc | accctgctct | gcctggcagt  1380 |
| aaaggtcacg | aattctggaa | acgagacttt | acaggcagca | gcgggctatt | ttcctttgtg  1440 |
| cttaagaaaa | aactcaataa | tgaagagctg | gcgaactatc | tggataactt | cagtttattc  1500 |
| agcatggcct | actcgtgggg | cgggtatgaa | tcgttgatcc | tggcaaatca | accagaacat  1560 |
| atcgccgcca | ttcgcccaca | aggcgagatc | gattttagcg | ggaccttgat | tcgcctgcat  1620 |
| attggtctgg | aagatgtcga | cgatctgatt | gccgatctgg | acgccggttt | tgcgcgaatt  1680 |
| gtataacatt | gccactttg | gacaattttg | cagacatttt | attgtgaaaa | gtcttaaatt  1740 |
| gttgcgtccg | ggatcaaggc | gtcccggacg | attcaggagt | acaataggca | gataaaggct  1800 |
| taaacgctgt | tccacaggaa | agtccatggc | tgttattcaa | gatatcatcg | ctgcgctctg  1860 |
| gcaacacgac | tttgccgcgc | | | |         1880 |

<210> SEQ ID NO 11
<211> LENGTH: 2083
<212> TYPE: DNA
<213> ORGANISM: Escherichia coli
<220> FEATURE:
<221> NAME/KEY: CDS
<222> LOCATION: (539)..(1954)
<223> OTHER INFORMATION:

<400> SEQUENCE: 11

| | |
|---|---:|
| gtaaaccgcg catacagccg cattctgact gtcagatgcg cttcgcttca ttgttaccgc | 60 |
| tcctgttatt cctcaaccct ttttttaaac attaaaattc ttacgtaatt tataatcttt | 120 |
| aaaaaaagca tttaatattg ctccccgaac gattgtgatt cgattcacat ttaaacaatt | 180 |
| tcagaataga caaaaactct gagtgtaata atgtagcctc gtgtcttgcg aggataagtg | 240 |
| cattatgaat atcttacata tatgtgtgac ctcaaaatgg ttcaatattg acaacaaaat | 300 |
| tgtcgatcac cgcccttgat ttgcccttct gtagccatca ccagagccaa accgattgat | 360 |
| tcaatgtgtt ctatttgttt gctatatctt aattttgcct tttgcaaagg tcatctctcg | 420 |
| tttatttact tgttttagta aatgatggtg cttgcatata tatctggcga attaatcggt | 480 |
| atagcagatg taatattcac aggatcact gtaattaaaa taaatgaagg attatgta | 538 |

| atg gaa aac ttt aaa cat ctc cct gaa ccg ttc cgc att cgt gtt att | 586 |
|---|---:|
| Met Glu Asn Phe Lys His Leu Pro Glu Pro Phe Arg Ile Arg Val Ile | |
| 1               5                   10                  15 | |

| gag cca gta aaa cgt acc act cgc gct tat cgt gaa gag gca att att | 634 |
|---|---:|
| Glu Pro Val Lys Arg Thr Thr Arg Ala Tyr Arg Glu Glu Ala Ile Ile | |
|             20                  25                  30 | |

| aaa tcc ggt atg aac ccg ttc ctg ctg gat agc gaa gat gtt ttt atc | 682 |
|---|---:|
| Lys Ser Gly Met Asn Pro Phe Leu Leu Asp Ser Glu Asp Val Phe Ile | |
|         35                  40                  45 | |

| gat tta ctg acc gac agc ggc acc ggg gcg gtg acg cag agc atg cag | 730 |
|---|---:|
| Asp Leu Leu Thr Asp Ser Gly Thr Gly Ala Val Thr Gln Ser Met Gln | |
|     50                  55                  60 | |

| gct gcg atg atg cgc ggc gac gaa gcc tac agc ggc agt cgt agc tac | 778 |
|---|---:|
| Ala Ala Met Met Arg Gly Asp Glu Ala Tyr Ser Gly Ser Arg Ser Tyr | |
| 65                  70                  75                  80 | |

| tat gcg tta gcc gag tca gtg aaa aat atc ttc ggt tat caa tac acc | 826 |
|---|---:|
| Tyr Ala Leu Ala Glu Ser Val Lys Asn Ile Phe Gly Tyr Gln Tyr Thr | |
|                 85                  90                  95 | |

| att ccg act cac cag ggc cgt ggc gca gag caa atc tat att ccg gta | 874 |
|---|---:|
| Ile Pro Thr His Gln Gly Arg Gly Ala Glu Gln Ile Tyr Ile Pro Val | |
|             100                 105                 110 | |

| ctg att aaa aaa cgc gag cag gaa aaa ggc ctg gat cgc agc aaa atg | 922 |
|---|---:|
| Leu Ile Lys Lys Arg Glu Gln Glu Lys Gly Leu Asp Arg Ser Lys Met | |
|         115                 120                 125 | |

| gtg gcg ttc tct aac tat ttc ttt gat acc acg cag ggc cat agc cag | 970 |
|---|---:|
| Val Ala Phe Ser Asn Tyr Phe Phe Asp Thr Thr Gln Gly His Ser Gln | |
|     130                 135                 140 | |

| atc aac ggc tgt acc gtg cgt aac gtc tat atc aaa gaa gcc ttc gat | 1018 |
|---|---:|
| Ile Asn Gly Cys Thr Val Arg Asn Val Tyr Ile Lys Glu Ala Phe Asp | |
| 145                 150                 155                 160 | |

| acg ggc gtg cgt tac gac ttt aaa ggc aac ttt gac ctt gag gga tta | 1066 |
|---|---:|
| Thr Gly Val Arg Tyr Asp Phe Lys Gly Asn Phe Asp Leu Glu Gly Leu | |
|                 165                 170                 175 | |

| gaa cgc ggt att gaa gaa gtt ggt ccg aat aac gtg ccg tat atc gtt | 1114 |
|---|---:|
| Glu Arg Gly Ile Glu Glu Val Gly Pro Asn Asn Val Pro Tyr Ile Val | |
|             180                 185                 190 | |

```
gca acc atc acc agt aac tct gca ggt ggt cag ccg gtt tca ctg gca    1162
Ala Thr Ile Thr Ser Asn Ser Ala Gly Gly Gln Pro Val Ser Leu Ala
            195                 200                 205 aac tta aaa gcg atg tac agc atc gcg aag aaa tac gat att ccg gtg    1210
Asn Leu Lys Ala Met Tyr Ser Ile Ala Lys Lys Tyr Asp Ile Pro Val
        210                 215                 220 gta atg gac tcc gcg cgc ttt gct gaa aac gcc tat ttc att aag cag    1258
Val Met Asp Ser Ala Arg Phe Ala Glu Asn Ala Tyr Phe Ile Lys Gln
225                 230                 235                 240 cgt gaa gca gaa tac aaa gac tgg acc atc gag cag atc acc cgc gaa    1306
Arg Glu Ala Glu Tyr Lys Asp Trp Thr Ile Glu Gln Ile Thr Arg Glu
                245                 250                 255 acc tac aaa tat gcc gat atg ctg gcg atg tcc gcc aag aaa gat gcg    1354
Thr Tyr Lys Tyr Ala Asp Met Leu Ala Met Ser Ala Lys Lys Asp Ala
            260                 265                 270 atg gtg ccg atg ggc ggc ctg ctg tgc atg aaa gac gac agc ttc ttt    1402
Met Val Pro Met Gly Gly Leu Leu Cys Met Lys Asp Asp Ser Phe Phe
        275                 280                 285 gat gtg tac acc gag tgc aga acc ctt tgc gtg gtg cag gaa ggc ttc    1450
Asp Val Tyr Thr Glu Cys Arg Thr Leu Cys Val Val Gln Glu Gly Phe
290                 295                 300 ccg aca tat ggc ggc cta gaa ggc ggc gcg atg gag cgt ctg gcg gta    1498
Pro Thr Tyr Gly Gly Leu Glu Gly Gly Ala Met Glu Arg Leu Ala Val
305                 310                 315                 320 ggt ctg tat gac ggc atg aat ctc gac tgg ctg gct tat cgt atc gcg    1546
Gly Leu Tyr Asp Gly Met Asn Leu Asp Trp Leu Ala Tyr Arg Ile Ala
                325                 330                 335 cag gta cag tat ctg gtc gat ggt ctg gaa gag att ggc gtt gtc tgc    1594
Gln Val Gln Tyr Leu Val Asp Gly Leu Glu Glu Ile Gly Val Val Cys
            340                 345                 350 cag cag gcg ggc ggt cac gcg gca ttc gtt gat gcc ggt aaa ctg ttg    1642
Gln Gln Ala Gly Gly His Ala Ala Phe Val Asp Ala Gly Lys Leu Leu
        355                 360                 365 ccg cat atc ccg gca gac cag ttc ccg gca aca ggc ctg gcc tgc gag    1690
Pro His Ile Pro Ala Asp Gln Phe Pro Ala Thr Gly Leu Ala Cys Glu
370                 375                 380 ctg tat aaa gtc gcc ggt atc cgt gcg gta gaa att ggc tct ttc ctg    1738
Leu Tyr Lys Val Ala Gly Ile Arg Ala Val Glu Ile Gly Ser Phe Leu
385                 390                 395                 400 tta ggc cgc gat ccg aaa acc ggt aaa caa ctg cca tgc ccg gct gaa    1786
Leu Gly Arg Asp Pro Lys Thr Gly Lys Gln Leu Pro Cys Pro Ala Glu
                405                 410                 415 ctg ctg cgt tta acc att ccg cgc gca aca tat act caa aca cat atg    1834
Leu Leu Arg Leu Thr Ile Pro Arg Ala Thr Tyr Thr Gln Thr His Met
            420                 425                 430 gac ttc att att gaa gcc ttt aaa cat gtg aaa gag aac gcg gcg aat    1882
Asp Phe Ile Ile Glu Ala Phe Lys His Val Lys Glu Asn Ala Ala Asn
        435                 440                 445 att aaa gga tta acc ttt acg tac gaa ccg aaa gta ttg cgt cac ttc    1930
Ile Lys Gly Leu Thr Phe Thr Tyr Glu Pro Lys Val Leu Arg His Phe
450                 455                 460 acc gca aaa ctt aaa gaa gtt taa ttaatactac agagtggcta taaggatgtt    1984
Thr Ala Lys Leu Lys Glu Val
465                 470 agccactctc ttaccctaca tcctcaataa caaaaatagc cttcctctaa aggtggcatc    2044
atgactgttc aagctgaaaa aaagcactct gcatttggg                          2083
```

<210> SEQ ID NO 12
<211> LENGTH: 471

```
<212> TYPE: PRT
<213> ORGANISM: Escherichia coli

<400> SEQUENCE: 12

Met Glu Asn Phe Lys His Leu Pro Glu Pro Phe Arg Ile Arg Val Ile
1               5                   10                  15

Glu Pro Val Lys Arg Thr Thr Arg Ala Tyr Arg Glu Ala Ile Ile
            20                  25                  30

Lys Ser Gly Met Asn Pro Phe Leu Asp Ser Glu Asp Val Phe Ile
            35                  40                  45

Asp Leu Leu Thr Asp Ser Gly Thr Gly Ala Val Thr Gln Ser Met Gln
50                  55                  60

Ala Ala Met Met Arg Gly Asp Glu Ala Tyr Ser Gly Ser Arg Ser Tyr
65                  70                  75                  80

Tyr Ala Leu Ala Glu Ser Val Lys Asn Ile Phe Gly Tyr Gln Tyr Thr
                85                  90                  95

Ile Pro Thr His Gln Gly Arg Gly Ala Glu Gln Ile Tyr Ile Pro Val
            100                 105                 110

Leu Ile Lys Lys Arg Glu Gln Glu Lys Gly Leu Asp Arg Ser Lys Met
            115                 120                 125

Val Ala Phe Ser Asn Tyr Phe Phe Asp Thr Thr Gln Gly His Ser Gln
130                 135                 140

Ile Asn Gly Cys Thr Val Arg Asn Val Tyr Ile Lys Glu Ala Phe Asp
145                 150                 155                 160

Thr Gly Val Arg Tyr Asp Phe Lys Gly Asn Phe Asp Leu Glu Gly Leu
                165                 170                 175

Glu Arg Gly Ile Glu Glu Val Gly Pro Asn Asn Val Pro Tyr Ile Val
            180                 185                 190

Ala Thr Ile Thr Ser Asn Ser Ala Gly Gly Gln Pro Val Ser Leu Ala
            195                 200                 205

Asn Leu Lys Ala Met Tyr Ser Ile Ala Lys Lys Tyr Asp Ile Pro Val
            210                 215                 220

Val Met Asp Ser Ala Arg Phe Ala Glu Asn Ala Tyr Phe Ile Lys Gln
225                 230                 235                 240

Arg Glu Ala Glu Tyr Lys Asp Trp Thr Ile Glu Gln Ile Thr Arg Glu
                245                 250                 255

Thr Tyr Lys Tyr Ala Asp Met Leu Ala Met Ser Ala Lys Lys Asp Ala
                260                 265                 270

Met Val Pro Met Gly Gly Leu Leu Cys Met Lys Asp Asp Ser Phe Phe
            275                 280                 285

Asp Val Tyr Thr Glu Cys Arg Thr Leu Cys Val Val Gln Glu Gly Phe
            290                 295                 300

Pro Thr Tyr Gly Gly Leu Glu Gly Gly Ala Met Glu Arg Leu Ala Val
305                 310                 315                 320

Gly Leu Tyr Asp Gly Met Asn Leu Asp Trp Leu Ala Tyr Arg Ile Ala
                325                 330                 335

Gln Val Gln Tyr Leu Val Asp Gly Leu Glu Glu Ile Gly Val Val Cys
            340                 345                 350

Gln Gln Ala Gly Gly His Ala Ala Phe Val Asp Ala Gly Lys Leu Leu
            355                 360                 365

Pro His Ile Pro Ala Asp Gln Phe Pro Ala Thr Gly Leu Ala Cys Glu
370                 375                 380

Leu Tyr Lys Val Ala Gly Ile Arg Ala Val Glu Ile Gly Ser Phe Leu
385                 390                 395                 400
```

```
Leu Gly Arg Asp Pro Lys Thr Gly Lys Gln Leu Pro Cys Pro Ala Glu
            405                 410                 415
Leu Leu Arg Leu Thr Ile Pro Arg Ala Thr Tyr Thr Gln Thr His Met
        420                 425                 430
Asp Phe Ile Ile Glu Ala Phe Lys His Val Lys Glu Asn Ala Ala Asn
    435                 440                 445
Ile Lys Gly Leu Thr Phe Thr Tyr Glu Pro Lys Val Leu Arg His Phe
450                 455                 460
Thr Ala Lys Leu Lys Glu Val
465                 470

<210> SEQ ID NO 13
<211> LENGTH: 1134
<212> TYPE: DNA
<213> ORGANISM: Escherichia coli
<220> FEATURE:
<221> NAME/KEY: CDS
<222> LOCATION: (223)..(1047)
<223> OTHER INFORMATION:

<400> SEQUENCE: 13
tccgcgaact ggcgcatcgc ttcggcgttg aaatgccaat aaccgaggaa atttatcaag      60
tattatattg cggaaaaaac gcgcgcgagg cagcattgac tttactaggt cgtgcacgca     120
aggacgagcg cagcagccac taaccccagg gaacctttgt taccgctatg acccggcccg     180
cgcagaacgg gccggtcatt atctcatcgt gtggagtaag ca atg tcg tgt gaa        234
                                              Met Ser Cys Glu
                                               1 gaa ctg gaa att gtc tgg aac aat att aaa gcc gaa gcc aga acg ctg        282
Glu Leu Glu Ile Val Trp Asn Asn Ile Lys Ala Glu Ala Arg Thr Leu
 5                  10                  15                  20 gcg gac tgt gag cca atg ctg gcc agt ttt tac cac gcg acg cta ctc        330
Ala Asp Cys Glu Pro Met Leu Ala Ser Phe Tyr His Ala Thr Leu Leu
                25                  30                  35 aag cac gaa aac ctt ggc agt gca ctg agc tac atg ctg gcg aac aag        378
Lys His Glu Asn Leu Gly Ser Ala Leu Ser Tyr Met Leu Ala Asn Lys
            40                  45                  50 ctg tca tcg cca att atg cct gct att gct atc cgt gaa gtg gtg gaa        426
Leu Ser Ser Pro Ile Met Pro Ala Ile Ala Ile Arg Glu Val Val Glu
        55                  60                  65 gaa gcc tac gcc gct gac ccg gaa atg atc gcc tct gcg gcc tgt gat        474
Glu Ala Tyr Ala Ala Asp Pro Glu Met Ile Ala Ser Ala Ala Cys Asp
    70                  75                  80 att cag gcg gtg cgt acc cgc gac ccg gca gtc gat aaa tac tca acc        522
Ile Gln Ala Val Arg Thr Arg Asp Pro Ala Val Asp Lys Tyr Ser Thr
85                  90                  95                 100 ccg ttg tta tac ctg aag ggt ttt cat gcc ttg cag gcc tat cgc atc        570
Pro Leu Leu Tyr Leu Lys Gly Phe His Ala Leu Gln Ala Tyr Arg Ile
                105                 110                 115 ggt cac tgg ttg tgg aat cag ggg cgt cgc gca ctg gca atc ttt ctg        618
Gly His Trp Leu Trp Asn Gln Gly Arg Arg Ala Leu Ala Ile Phe Leu
            120                 125                 130 caa aac cag gtt tct gtg acg ttc cag gtc gat att cac ccg gca gca        666
Gln Asn Gln Val Ser Val Thr Phe Gln Val Asp Ile His Pro Ala Ala
        135                 140                 145 aaa att ggt cgc ggt atc atg ctt gac cac gcg aca ggc atc gtc gtt        714
Lys Ile Gly Arg Gly Ile Met Leu Asp His Ala Thr Gly Ile Val Val
    150                 155                 160 ggt gaa acg gcg gtg att gaa aac gac gta tcg att ctg caa tct gtg        762
```

```
Gly Glu Thr Ala Val Ile Glu Asn Asp Val Ser Ile Leu Gln Ser Val
165                 170                 175                 180 acg ctt ggc ggt acg ggt aaa tct ggt ggt gac cgt cac ccg aaa att      810
Thr Leu Gly Gly Thr Gly Lys Ser Gly Gly Asp Arg His Pro Lys Ile
                185                 190                 195 cgt gaa ggt gtg atg att ggc gcg ggc gcg aaa atc ctc ggc aat att      858
Arg Glu Gly Val Met Ile Gly Ala Gly Ala Lys Ile Leu Gly Asn Ile
            200                 205                 210 gaa gtt ggg cgc ggc gcg aag att ggc gca ggt tcc gtg gtg ctg caa      906
Glu Val Gly Arg Gly Ala Lys Ile Gly Ala Gly Ser Val Val Leu Gln
        215                 220                 225 ccg gtg ccg ccg cat acc acc gcc gct ggc gtt ccg gct cgt att gtc      954
Pro Val Pro Pro His Thr Thr Ala Ala Gly Val Pro Ala Arg Ile Val
    230                 235                 240 ggt aaa cca gac agc gat aag cca tca atg gat atg gac cag cat ttc     1002
Gly Lys Pro Asp Ser Asp Lys Pro Ser Met Asp Met Asp Gln His Phe
245                 250                 255                 260 aac ggt att aac cat aca ttt gag tat ggg gat ggg atc taa tgt         1047
Asn Gly Ile Asn His Thr Phe Glu Tyr Gly Asp Gly Ile     Cys
                265                 270 cctgtgatcg tgccggatgc gatgtaatca tctatccggc ctacagtaac taatctctca   1107
ataccgctcc cgataccca actgtcg                                         1134

<210> SEQ ID NO 14
<211> LENGTH: 273
<212> TYPE: PRT
<213> ORGANISM: Escherichia coli

<400> SEQUENCE: 14

Met Ser Cys Glu Glu Leu Glu Ile Val Trp Asn Asn Ile Lys Ala Glu
1               5                   10                  15

Ala Arg Thr Leu Ala Asp Cys Glu Pro Met Leu Ala Ser Phe Tyr His
            20                  25                  30

Ala Thr Leu Leu Lys His Glu Asn Leu Gly Ser Ala Leu Ser Tyr Met
        35                  40                  45

Leu Ala Asn Lys Leu Ser Ser Pro Ile Met Pro Ala Ile Ala Ile Arg
    50                  55                  60

Glu Val Val Glu Glu Ala Tyr Ala Ala Asp Pro Glu Met Ile Ala Ser
65                  70                  75                  80

Ala Ala Cys Asp Ile Gln Ala Val Arg Thr Arg Asp Pro Ala Val Asp
                85                  90                  95

Lys Tyr Ser Thr Pro Leu Leu Tyr Leu Lys Gly Phe His Ala Leu Gln
            100                 105                 110

Ala Tyr Arg Ile Gly His Trp Leu Trp Asn Gln Gly Arg Arg Ala Leu
        115                 120                 125

Ala Ile Phe Leu Gln Asn Gln Val Ser Val Thr Phe Gln Val Asp Ile
    130                 135                 140

His Pro Ala Ala Lys Ile Gly Arg Gly Ile Met Leu Asp His Ala Thr
145                 150                 155                 160

Gly Ile Val Val Gly Glu Thr Ala Val Ile Glu Asn Asp Val Ser Ile
                165                 170                 175

Leu Gln Ser Val Thr Leu Gly Gly Thr Gly Lys Ser Gly Gly Asp Arg
            180                 185                 190

His Pro Lys Ile Arg Glu Gly Val Met Ile Gly Ala Gly Ala Lys Ile
        195                 200                 205

Leu Gly Asn Ile Glu Val Gly Arg Gly Ala Lys Ile Gly Ala Gly Ser
```

```
                    210                 215                 220

Val Val Leu Gln Pro Val Pro Pro His Thr Thr Ala Ala Gly Val Pro
225                 230                 235                 240

Ala Arg Ile Val Gly Lys Pro Asp Ser Asp Lys Pro Ser Met Asp Met
                245                 250                 255

Asp Gln His Phe Asn Gly Ile Asn His Thr Phe Glu Tyr Gly Asp Gly
                260                 265                 270

Ile
```

L-CYSTEINE PRODUCING BACTERIUM AND METHOD FOR PRODUCING L-CYSTEINE

BACKGROUND OF THE INVENTION

1. Field of the Invention

The present invention relates to a method for producing L-cysteine. More precisely, it relates to a microorganism suitable for the production of L-cysteine and a method for producing L-cysteine utilizing such a microorganism. L-Cysteine and L-cysteine derivatives are used in the fields of drugs, cosmetics and foods.

2. Related Art

L-Cysteine is conventionally obtained by extracting it from keratin-containing substances such as hairs, horns and feathers or conversion of DL-2-aminothiazoline-4-carboxylic acid as a precursor using a microbial enzyme. It is also planned to produce L-cysteine in a large scale by an immobilized enzyme method utilizing a novel enzyme.

Furthermore, it is also attempted to produce L-cysteine by fermentation utilizing a microorganism. For example, the inventors of the present invention disclosed a method for producing L-cysteine by using a bacterium belonging to the genus *Escherichia* having serine acetyltransferase (EC 2.3.1.30, also referred to as "SAT" hereinafter) in which L-cysteine decomposition system is suppressed and feedback inhibition by L-cysteine is reduced (Japanese Patent Laid-open Publication (Kokai) No. 11-155571). As means for suppressing the L-cysteine decomposition system, reduction of intracellular cysteine desulfhydrase (also referred to as "CD" herein after) activity is disclosed. There is also known a method for producing L-cysteine by using a microorganism of which cysteine metabolism is decontrolled by using a DNA sequence coding for SAT that has a specific mutation so as to reduce feedback inhibition by L-cysteine (International Patent Publication in Japanese (Kohyo) No. 2000-504926).

Further, FEMS Microbiol. Lett., 179, 453–459 (1999) discloses a method for producing L-cysteine by using *Escherichia coli* introduced with a gene coding for an SAT isozyme derived from *Arabidopsis thaliana*, which does not suffer from feedback inhibition by L-cysteine.

Moreover, Japanese Patent Laid-open Publication No. 11-56381 discloses a method for producing L-cysteine using a microorganism overexpressing a gene coding for a protein suitable for releasing an antibiotic or a substance toxic to a microorganism directly from a cell.

As described above, various researches have been made about enhancement of activities of L-cysteine biosynthesis enzymes such as SAT and L-cysteine producing bacteria of which L-cysteine excretory system is modified. However, the L-cysteine decomposition system has not been studied in detail, in particular, for bacteria belonging to the genus *Escherichia*.

As enzymes somewhat showing CD activity in *Escherichia coli*, there have been reported cystathionine-β-lyase (metC product, also referred to as "CBL" hereinafter, Chandra et al., Biochemistry, 21, 3064–3069 (1982)) and tryptophanase (tnaA product, also referred to as "TNase", Austin Newton et al., J. Biol. Chem., 240, 1211–1218 (1965)). However, it is considered that CBL and TNase are enzymes catalyzing a reaction of converting cystathionine into homocysteine and a reaction of decomposing tryptophan, respectively, and it is not known whether they are enzymes substantially involved in the L-cysteine decomposition system. Further, although a mutant strain showing reduced CD activity is disclosed in Japanese Patent Laid-open Publication No. 11-155571, it does not report identity of the enzyme responsible for the CD activity.

SUMMARY OF THE INVENTION

An object of the present invention is to elucidate enzymes responsible for the CD activity and genes therefor and utilize such genes for breeding of L-cysteine producing bacteria to provide a novel method of producing L-cysteine.

The inventors of the present invention have made extensive studies in order to achieve the aforementioned object. As a result, they found that CBL and TNase were major enzymes responsible for the CD activity of *Escherichia coli*, and that L-cysteine producing ability can be improved by reducing or eliminating the activities of these enzymes. Thus, they accomplished the present invention.

That is, the present invention provides the followings.

(1) A bacterium belonging to the genus *Escherichia* having an L-cysteine producing ability and modified so that cystathionine-β-lyase activity should be reduced or eliminated.

(2) A bacterium belonging to the genus *Escherichia* having an L-cysteine producing ability and modified so that cystathionine-β-lyase activity and tryptophanase activity should be reduced or eliminated.

(3) The bacterium belonging to the genus *Escherichia* according to (1), wherein a gene coding for cystathionine-β-lyase is disrupted.

(4) The bacterium belonging to the genus *Escherichia* according to (2), wherein genes coding for cystathionine-β-lyase and tryptophanase are disrupted.

(5) The bacterium according to any one of (1) to (4), which is further modified so that activity of one or more enzymes of L-cysteine biosynthetic pathway should be enhanced.

(6) The bacterium belonging to the genus *Escherichia* according to (5), which is modified so that serine acetyltransferase should be enhanced.

(7) The bacterium belonging to the genus *Escherichia* according to (6), in which feedback inhibition of acetyltransferase by L-cysteine is desensitized.

(8) The bacterium belonging to the genus *Escherichia* according to any one of (1) to (7), which is *Escherichia coli*.

(9) A method for producing L-cysteine, which comprises culturing the bacterium belonging to the genus *Escherichia* according to any one of (1) to (8) in a medium to produce and accumulate L-cysteine in the medium and collecting the L-cysteine from the medium.

(10) A method for producing an L-cysteine producing bacterium, which comprises reducing or eliminating either one or both of cystathionine-β-lyase activity and tryptophanase activity of a bacterium belonging to the genus *Escherichia* to enhance an L-cysteine producing ability of the bacterium.

In the present invention, the term "the L-cysteine producing ability" means an ability of the bacterium belonging to the genus *Escherichia* of the present invention to accumulate L-cysteine in a medium in such an amount that the L-cysteine can be collected from the medium when the bacterium is cultured in the medium. Further, the term "insensitive to feedback inhibition by L-cysteine" includes a case where an enzyme originally does not suffer from the feedback inhibition as well as a case where the feedback inhibition by L-cysteine is reduced or eliminated.

In addition, the term L-cysteine used in the present invention means reduced type L-cysteine, L-cystine or a mixture thereof, unless otherwise specified.

PREFERRED ENBODIMENTS OF THE INVENTION

Figure 1:
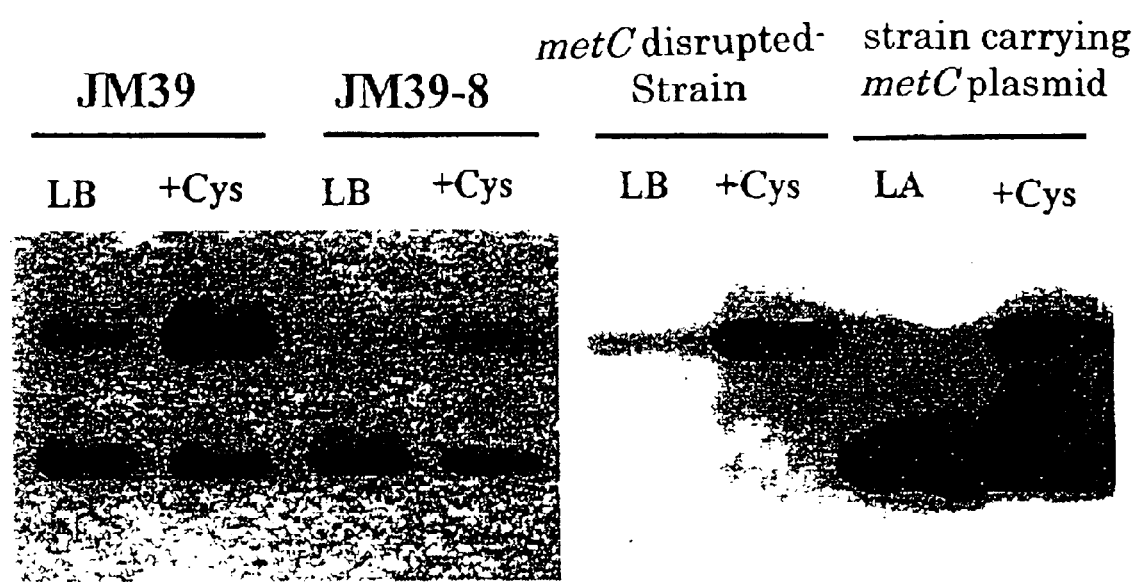
FIG. 1 shows results of CD activity staining of *Escherichia coli* cell extract after Native-PAGE. A: SAT-deficient strain, JM39, and CD activity-reduced strain, JM39-8, B: metC-deficient strain, EZ5, and EZ5 introduced with plasmid pIP29 carrying metC.

A first aspect of the bacterium belonging to the genus *Escherichia* of the present invention is a bacterium belonging to the genus *Escherichia* which has an ability to produce L-cysteine and which is modified so that the CBL activity should be reduced or eliminated. A second aspect of the bacterium belonging to the genus *Escherichia* of the present invention is a bacterium belonging to the genus *Escherichia* which has an ability to produce L-cysteine and which is modified so that the CBL activity and TNase activity should be reduced or eliminated. Further, the bacterium belonging to the genus *Escherichia* of the present invention may be the bacterium belonging to the genus *Escherichia* according to the aforementioned first or second aspect, which is further modified so that activity of enzyme(s) of L-cysteine biosynthetic pathway should be enhanced. Such a bacterium belonging to the genus *Escherichia* can be obtained by enhancing activity of one or more enzymes of L-cysteine biosynthetic pathway in a bacterium belonging to the genus *Escherichia* in which the CBL activity, or CBL activity and TNase activity are reduced or eliminated. Further, such a bacterium belonging to the genus *Escherichia* of the present invention can also be obtained by reducing or eliminating the CBL activity or CBL activity and TNase activity in a bacterium belonging to the genus *Escherichia* in which activity of enzyme(s) of L-cysteine biosynthetic pathway is enhanced.

<1>Reduction or Elimination of CBL Activity or TNase Activity

To reduce or eliminate the CBL activity or TNase activity of a bacterium belonging to the genus *Escherichia*, there can be used, for example, a method of treating a bacterium belonging to the genus *Escherichia* with ultraviolet irradiation or a mutagen used for ordinary mutagenesis treatment such as N-methyl-N'-nitro-N-nitrosoguanidine (NTG) or nitrous acid and selecting a mutant strain in which the CBL activity or TNase activity is reduced. Alternatively, a bacterium belonging to the genus *Escherichia* in which the CBL activity or TNase activity is reduced can also be obtained by gene disruption, besides the mutagenesis treatment. In order to surely reduce or eliminate the CBL activity or TNase activity, a method based on the gene disruption is preferred. In *Escherichia coli*, CBL and TNase are encoded by metC gene and tnaA gene, respectively.

For *Escherichia coli*, there were reported nucleotide sequences of the metC gene (GenBank accession M12858, Proc. Natl. Acad. Sci. U.S.A., 83, 867–871 (1986)) and tnaA gene (GenBank accession K00032, J. Bacteriol., 147, 787–796, (1981); J. Bacteriol., 151, 942–951 (1982)), and a DNA fragment containing each gene can be obtained by PCR (polymerase chain reaction; refer to White, T. J. et al., Trends Genet., 5, 185 (1989)) using primers synthesized based on each sequence and *Escherichia coli* chromosomal DNA as a template. Further, a metC gene modified so as not to produce CBL that normally functions by deletion of an internal sequence of a gene coding for CBL (deletion type metC gene) and a tnaA gene modified so as not to produce TNase that normally functions by deletion of an internal sequence of a gene coding for TNase (deletion type tnaA gene) can be obtained by PCR using primers mentioned in the examples.

For reference, the nucleotide sequence of metC gene and the encoded amino acid sequence are shown as SEQ ID NOS: 10 and 11. The nucleotide sequence of tnaA gene and the encoded amino acid sequence are shown as SEQ ID NOS: 12 and 13.

A method of disrupting a gene coding for CBL will be explained below. A gene coding for TNase can be disrupted in a similar manner.

A bacterium belonging to the genus *Escherichia* can be transformed with DNA containing a metC gene modified with deletion of internal sequence of the gene coding for CBL so as not to produce CBL that functions normally (deletion type metC gene), so that recombination between the deletion type metC gene and the metC gene on the chromosome should occur, to disrupt the metC gene on the chromosome. Such gene disruption by gene substitution utilizing homologous recombination has already been established, and there are methods utilizing a linear DNA, a plasmid that contains a temperature sensitive replication origin and so forth.

A metC gene on host chromosome can be replaced with the deletion type metC gene, for example, as follows. That is, a recombinant DNA is prepared by inserting a temperature sensitive replication origin, a deletion type metC gene and a marker gene for resistance to a drug such as ampicillin or chloramphenicol into a vector, and a bacterium belonging to the genus *Escherichia* is transformed with the recombinant DNA. Further, the resultant transformant strain is cultured at a temperature at which the temperature sensitive replication origin does not function, and then the transformant strain is cultured in a medium containing the drug to obtain a transformant strain in which the recombinant DNA is incorporated into the chromosomal DNA.

In such a strain in which the recombinant DNA is incorporated into the chromosomal DNA as described above, the deletion type metC gene is recombined with the metC gene originally present on the chromosome, and the two fusion genes of the chromosomal metC gene and the deletion type metC gene are inserted into the chromosome so that the other portions of the recombinant DNA (vector segment, temperature sensitive replication origin and drug resistance marker) should be present between the two fusion genes. Therefore, the transformant strain expresses normal CBL, because the normal metC gene is dominant in this state.

Then, in order to leave only the deletion type metC gene on the chromosomal DNA, one copy of the metC gene is eliminated together with the vector segment (including the temperature sensitive replication origin and the drug resistance marker) from the chromosomal DNA by recombination of two of the metC genes. In this case, the normal metC gene is left on the chromosomal DNA and the deletion type metC gene is excised from the chromosomal DNA, or to the contrary, the deletion type metC gene is left on the chromosomal DNA and the normal metC gene is excised from the chromosome DNA. In the both cases, the excised DNA may be harbored in the cell as a plasmid when the cell is cultured at a temperature at which the temperature sensitive replication origin can function. Subsequently, if the cell is cultured at a temperature at which the temperature sensitive replication origin cannot function, the metC gene on the plasmid is eliminated together with the plasmid from the cell. Then, a strain in which metC gene is disrupted can be obtained by selecting a strain in which the deletion type metC gene is left on the chromosome using PCR, Southern hybridization or the like.

Reduction or elimination of the CBL activity in a gene-disrupted strain or mutant strain can be confirmed by measuring the CBL activity of cell extract of a candidate strain by the method of Guggenheim, S. (Methods Enzymol., 17, 439–442 (1971)) or the like and comparing it with the CBL activity of the parent strain.

Examples of the plasmid including a temperature sensitive replication origin for *Escherichia coli* include, for example, pMAN031 (Yasueda, H. et al, Appl. Microbiol. Biotechnol., 36, 211 (1991)), pMAN997 (WO99/03988) and pEL3 (K. A. Armstrong et al., J. Mol. Biol., 175, 331–347 (1984)).

In a manner similar to the above, a tnaA gene-disrupted strain can be obtained. Reduction or elimination of the TNase activity in a tnaA gene-disrupted strain or mutant strain can be confirmed by measuring the TNase activity of cell extract of a candidate strain by the method of Newton, W. A. et al. (J. Biol. Chem., 240, 1211–1218 (1965)) or the like and comparing it with the TNase activity of the parent strain.

It is sufficient that the deletion type metC gene and the deletion type tnaA gene used for the gene disruption should have homology to a metC gene and tnaA gene on chromosomal DNA of *Escherichia* bacterium, respectively, in such a degree that they should cause homologous recombination with them. Such homology is preferably 70% or more, more preferably 80% or more, particularly preferably 90% or more. Further, DNA's hybridizable under a stringent condition may cause homologous recombination.

<2>Enhancement of SAT Activity

Enhancement of the SAT activity in a cell of a bacterium belonging to the genus *Escherichia* can be attained by increasing copy number of a gene coding for SAT. For example, a recombinant DNA can be prepared by ligating a gene fragment coding for SAT with a vector that functions in bacteria belonging to the genus *Escherichia*, preferably a multi-copy type vector, and introduced into a host bacterium belonging to the genus *Escherichia* to transform it.

As the SAT gene, any of genes derived from bacteria belonging to the genus *Escherichia* and genes derived from other organisms can be used. As the gene coding for SAT of *Escherichia coli*, cysE has been cloned from a wild strain and an L-cysteine secretion mutant strain, and the nucleotide sequence has been elucidated (Denk, D. and Boeck, A., J. General Microbiol., 133, 515–525 (1987)). Therefore, a SAT gene can be obtained by PCR utilizing primers prepared based on the nucleotide sequence and chromosomal DNA of *Escherichia* bacterium as a template (refer to Japanese Patent Laid-open Publication No. 11-155571). Genes coding for SAT of other microorganisms can also be obtained in a similar manner.

For reference, the reported nucleotide sequence of wild-type cysE and the encoded amino acid sequence of SAT (Denk, D. and Bock, A., J. General Microbiol., 133, 515–525 (1987)) are shown as SEQ ID NOS: 14 and 15.

Besides a wild-type SAT gene, the SAT gene may be one coding for an amino acid sequence including substitution, deletion, insertion, addition or inversion of one or more amino acid residues that does not substantially degrade the activity for catalyzing the activation of L-serine by acetyl-CoA. Although the number of "several" amino acid residues referred to herein differs depending on position or type of amino acid residues in the three-dimensional structure of the protein, it may be preferably 2 to 50, more preferably 2 to 40, patricularly preferably 2 to 30. The "stringent condition" may be a condition under which a so-called specific hybrid is formed, and a non-specific hybrid is not formed. It is difficult to clearly express this condition by using any numerical value. However, for example, the stringent condition is exemplified by a condition under which DNA's having high homology, for example, DNA's having homology of 50% or more are hybridized with each other, but DNA's having homology lower than the above are not hybridized with each other. Alternatively, the stringent condition is exemplified by a condition under which DNA's are hybridized with each other at a salt concentration corresponding to an ordinary condition of washing in Southern hybridization, i.e., 1×SSC, 0.1% SDS, preferably 0.1×SSC, 0.1% SDS, at 60° C.

As such DNA coding for a protein substantially identical to SAT as described above, there can be mentioned DNA that is hybridizable with a nucleotide sequence comprising the sequence of the nucleotide numbers 223 to 1047 in SEQ ID NO: 14 or a probe that can be produced from the nucleotide sequence under a stringent condition and codes for a protein having an activity similar to that of SAT.

The chromosomal DNA can be prepared from a bacterium, which is a DNA donor, by the method of Saito and Miura (refer to H. Saito and K. Miura, Biochem. Biophys. Acta, 72, 619 (1963); Text for Bioengineering Experiments, Edited by the Society for Bioscience and Bioengineering, Japan, pp.97–98, Baifukan, 1992), for example.

In order to introduce a DNA fragment containing SAT gene amplified by PCR into a bacterium belonging to the genus *Escherichia*, various vectors used for usual protein expression can be used. Examples of such vectors include pUC19, pUC18, pHSG299, pHSG399, pHSG398, RSF1010, pBR322, pACYC184, pMW219 and so forth.

Introduction of a recombinant vector containing the SAT gene into *Escherichia* bacterium can be attained by methods usually used for transformation of bacteria belonging to the genus *Escherichia*, for example, the method of D. A. Morrison (Methods in Enzymology, 68, 326 (1979)), a method of treating recipient cells with calcium chloride so as to increase the permeability for DNA (Mandel, M. and Higa, A., J. Mol. Biol., 53, 159 (1970)) and so forth.

Increase of copy number of the SAT gene can also be achieved by introducing multiple copies of the SAT gene into chromosomal DNA of a bacterium belonging to the genus *Escherichia*. In order to introduce multiple copies of the SAT gene into chromosomal DNA of a bacterium belonging to the genus *Escherichia*, homologous recombination is carried out by using a sequence whose multiple copies exist in the chromosomal DNA as a target. As sequences whose multiple copies exist in chromosomal DNA, repetitive DNA or inverted repeat existing at the ends of a transposable element can be used. Further, as disclosed in Japanese Patent Laid-open Publication No. 2-109985, it is also possible to incorporate the SAT gene into transposon, and allow it to be transferred to introduce multiple copies of the gene into chromosomal DNA.

The amplification of the SAT activity can also be attained by, besides being based on the aforementioned gene amplification, replacing an expression regulatory sequence such as a promoter of the SAT gene of chromosomal DNA or plasmid with a stronger one (refer to Japanese Patent Laid-open Publication No. 1-215280). For example, lac promoter, trp promoter, trc promoter and so forth are known as strong promoters. Substitution of expression regulatory sequence can also be attained by, for example, gene substitution utilizing temperature sensitive plasmid.

Furthermore, it is also possible to introduce nucleotide substitution for several nucleotides in the promoter region of the SAT gene to modify the promoter into a stronger one as disclosed in International Patent Publication WO00/18935. Expression of the SAT gene is enhanced by such substitution or modification of the promoter and thus the SAT activity is enhanced. These modifications of expression regulatory sequence may be combined with increase of copy number of the SAT gene.

Furthermore, when a suppression mechanism exists for the expression of the SAT gene, expression of the SAT gene can also be enhanced by modifying an expression regulatory sequence or a gene involved in the suppression so that the suppression should be eliminated or reduced.

The intracellular SAT activity of a bacterium belonging to the genus *Escherichia* can be also increased by making a bacterium belonging to the genus *Escherichia* contain SAT of which feedback inhibition by L-cysteine is reduced or eliminated (henceforth also referred to as "mutant type SAT"). Examples of the mutant type SAT include SAT having a mutation for replacing an amino acid residue corresponding to the methionine residue at a positon 256 of a wild-type SAT with an amino acid residue other than lysine residue and leucine residue, or a mutation for deleting a C-terminal region from an amino acid residue corresponding to the methionine residue at a position 256. Examples of the amino acid residue other than lysine residue and leucine residue include the 17 kinds of amino acid residues among the amino acids constituting ordinary proteins except for methionine residue, lysine residue and leucine residue. More specifically, isoleucine residue can be mentioned. As a method of introducing a desired mutation into a wild-type SAT gene, site-specific mutagenesis can be mentioned. As a mutant type SAT gene, a mutant type cysE coding for a mutant type SAT of *Escherichia coli* is known (refer to International Patent Publication WO97/15673 and Japanese Patent Laid-open Publication No. 11-155571). *Escherichia coli* JM39-8 strain harboring a plasmid pCEM256E containing a mutant type cysE coding for a mutant type SAT in which the methionine residue at a position 256 is replaced with a glutamic acid residue (*E. coli* JM39-8(pCEM256E), private number: AJ13391) has been deposited at the National Institute of Bioscience and Human-Technology, Agency of Industrial Science and Technology (currently, National Institute of Advanced Industrial Science and Technology, International Patent Organism Depositary, Central 6, 1-1, Higashi 1-Chome, Tsukuba-shi, Ibaraki-ken, 305-8566, Japan) since Nov. 20, 1997 under the accession number of FERM P-16527. The original deposit was converted to the international deposit based on Budapest Treaty on Jul. 8, 2002, and given the accession number of FERM BP-8112.

Further, SAT of *Arabidopsis thaliana* is known not to suffer from the feedback inhibition by L-cysteine and can be suitably used for the present invention. As a plasmid containing SAT gene derived from *Arabidopsis thaliana*, pEAS-m is known (FEMS Microbiol. Lett., 179 453–459 (1999)).

The mutant type SAT may be one having an amino acid sequence including such substitution, deletion, insertion, addition or inversion of one or several amino acid residues that the activity for catalyzing the activation of L-serine with acetyl-CoA should not be substantially degraded, in addition to the aforementioned mutation that reduces feedback inhibition by L-cysteine. In SAT having such a mutation, the position of the 256th methionine residue may be changed. Even in such a case, a mutant type SAT of which feedback inhibition by L-cysteine is reduced can be obtained by replacing an amino acid residue corresponding to the 256th methionine residue with an amino acid residue other than lysine residue and leucine residue.

Further, a bacterium belonging to the genus *Escherichia* can be made contain a mutant type SAT by introducing such a mutation that the feedback inhibition of the encoded SAT by L-cysteine should be eliminated into the intracellular SAT gene. Such a mutation can be introduced by a treatment with ultraviolet irradiation or a mutagenizing agent used for usual mutagenesis treatment such as N-methyl-N'-nitro-N-nitrosoguanidine (NTG) or nitrous acid.

<3>Production of L-Cysteine

L-Cysteine can be efficiently and stably produced by culturing the bacterium belonging to the genus *Escherichia* of the present invention that can be obtained as described above in a suitable medium to produce and accumulate L-cysteine in the culture and collecting the L-cysteine from the culture. Although L-cysteine produced by the method of the present invention may contain cystine in addition to reduced type cysteine, the object of the production method of the present invention include cystine and a mixture of reduced type cysteine and cystine.

As the medium used, ordinary media containing a carbon source, nitrogen source, sulfur source, inorganic ions and other organic components as required can be mentioned.

As the carbon source, saccharides such as glucose, fructose, sucrose, molasses and starch hydrolysate, organic acids such as fumaric acid, citric acid and succinic acid can be used.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the sulfur source, inorganic sulfur compounds, such as sulfates, sulfites, sulfides, hyposulfites and thiosulfates can be mentioned.

As organic trace amount nutrients, it is desirable to add required substances such as vitamin $B_1$, yeast extract and so forth in appropriate amounts. Other than these, potassium phosphate, magnesium sulfate, iron ions, manganese ions and so forth are added in small amounts.

The culture is preferably performed under an aerobic condition for 30 to 90 hours. The culture temperature is controlled to be at 25° C. to 37° C., and pH is controlled to be 5 to 8 during the culture. For pH adjustment, inorganic or organic acidic or alkaline substances, ammonia gas and so forth can be used. Collection of L-cysteine from the culture can be attained by, for example, a combination of ordinary ion exchange resin method, precipitation and other known methods.

EXAMPLES

Hereafter, the present invention will be explained more specifically with reference to the,following examples.

9

<1>Identification of Enzyme Having CD Activity in *Escherichia coli*
(1) Electrophoresis and CD Activity Staining of *Escherichia coli* Cell Extract Cell extracts of *Escherichia coli* JM39 (F$^+$ cysE51 tfr-8, Denk, D. and Bock, A., J. Gene. Microbiol, 133, 515–525 (1987)), which is a SAT-deficient strain of *Escherichia coli*, and a CD activity reduced strain, JM39-8 (Japanese Patent Laid-open Publication No. 11-155571) were subjected to non-denatured polyacrylamide gel electrophoresis (Native-PAGE) and CD activity staining to analyze the entity of the CD activity. The JM39-8 strain is a mutant strain separated as an L-cysteine non-assimilating strain from cells of the JM39 strain subjected to an NTG treatment (Japanese Patent Laid-open Publication No. 11-155571).

Each strain was inoculated into LB medium (10 g/L of trypton, 5 g/L of yeast extract, 5 g/L of NaCl (pH 7.0)) added or not added with 0.3% of L-cysteine and cultured overnight at 37° C. The cells were collected by centrifugation and washed with 0.85% NaCl, and the obtained wet cells were suspended in about 3 ml of a buffer for cell disruption (10 mM Tris-HCl (pH8.6), 10 $\mu$M PLP, 100 $\mu$M DTT) and subjected to cell disruption by ultrasonication for 30 minutes on Bioruptor (COSMOBIO). The cell disruption suspension was centrifuged at 12,000 rpm for 10 minutes to obtain a cell extract as the supernatant. Protein concentration of the extract was determined by using Protein Assay Kit (Bio-Rad).

Each cell extract (30 $\mu$g protein for each) was suspended in 2×Native-PAGE buffer (14.43 g/L of glycine, 3.0 g/L of Tris, pH 8.6 (HCl)) and subjected to non-denatured polyacrylamide gel electrophoresis (Native-PAGE) in a conventional manner. The obtained electrophoresis gel was subjected to CD activity staining. Only the lanes of the both sides of the gel were excised and immersed in a reaction solution (prepared as 100 mM Tris-HCl, 10 mM EDTA, 20 $\mu$M PLP (pyridoxal-5-phosphate), 50 mM L-Cys, pH 8.6, then filled up to 100 ml and added with 50 mg of bismuth chloride (BiCl$_3$)), and left at room temperature with shaking until bands appeared. As a result, two major bands were detected (FIG. 1A). The lanes at the center of the gel were used for amino acid sequence determination. The larger molecular weight band of the JM39-8 strain among two of the bands was weaker than that of the JM39 strain.

(2) Identification of CBL as Enzyme Having CD Activity

As an enzyme having the CD activity in *Escherichia coli*, CBL (metC product) was reported (Chandra et al., Biochemistry, 21, 3064–3069 (1982)). In order to verify that the aforementioned band was CBL, the same experiment as described above was carried out by using a metC-deficient strain and *Escherichia coli* of which metC gene was amplified by using a multicopy plasmid.

By using a metC-deficient strain EZ5 (metC: Tn10Tet$^s$ rpsL add-uid-man uraA:Tn10) and EZ5 introduced with a plasmid pIP29 carrying metC (provided from Dr. Saint-Girons, Pasteur Institute, France, refer to Belfaiza et al., Proc. Natl. Acad. Sci., 83, 867–871 (1986)), Native-PAGE and CD activity staining were performed. As a result, it was found that the band of the smaller molecular weight was deleted in the metC-deficient strain, and that the band was significantly amplified by introduction of pIP29 (FIG. 1B). Based on this result, it was concluded that the band of the smaller molecular weight was CBL.

(3) Identification of TNase as Enzyme Having CD Activity

The protein of the band of the larger molecular weight among the two of the aforementioned bands observed in the activity staining was purified. The band of the larger molecular weight was excised from the electrophoresis gel, then extracted and concentrated in a conventional manner. The obtained fraction having the CD activity was subjected to SDS-polyacrylamide gel electrophoresis (SDS-PAGE) and blotted to a PVDF membrane (Bio-Rad) without staining. The membrane after the blotting was washed with distilled water and stained for 5 minutes with 40% methanol containing 0.025% CBB (Coomassie Brilliant Blue) R-250. Decoloration was performed with 50% methanol, and a confirmed band of the target enzyme was excised. The N-terminus amino acid sequence of the enzyme was determined by the automatic Edman degradation method using Protein Sequencer 476A (Applied Biosystems).

The result is shown as SEQ ID NO: 1. This sequence was compared with the amino acid sequence of TNase of *Escherichia coli*, which was reported to have weak CD activity (Austin Newton et al., J. Biol. Chem., 240, 1211–1218 (1965)), and it was found that 14 residues among the 15 residues were identical. The methionine residue at the 10th position of the amino acid sequence of SEQ ID NO: 1 was proline residue in the reported amino acid sequence. Based on this result, it was thought that the band of the larger molecular weight was highly possibly TNase. It was also assumed based on this result that the expression of TNase was reduced in the JM39-8 strain.

<2>Construction of tnaA-Deficient Strain and metC-Deficient Strain of *Escherichia coli*

Figure 2:
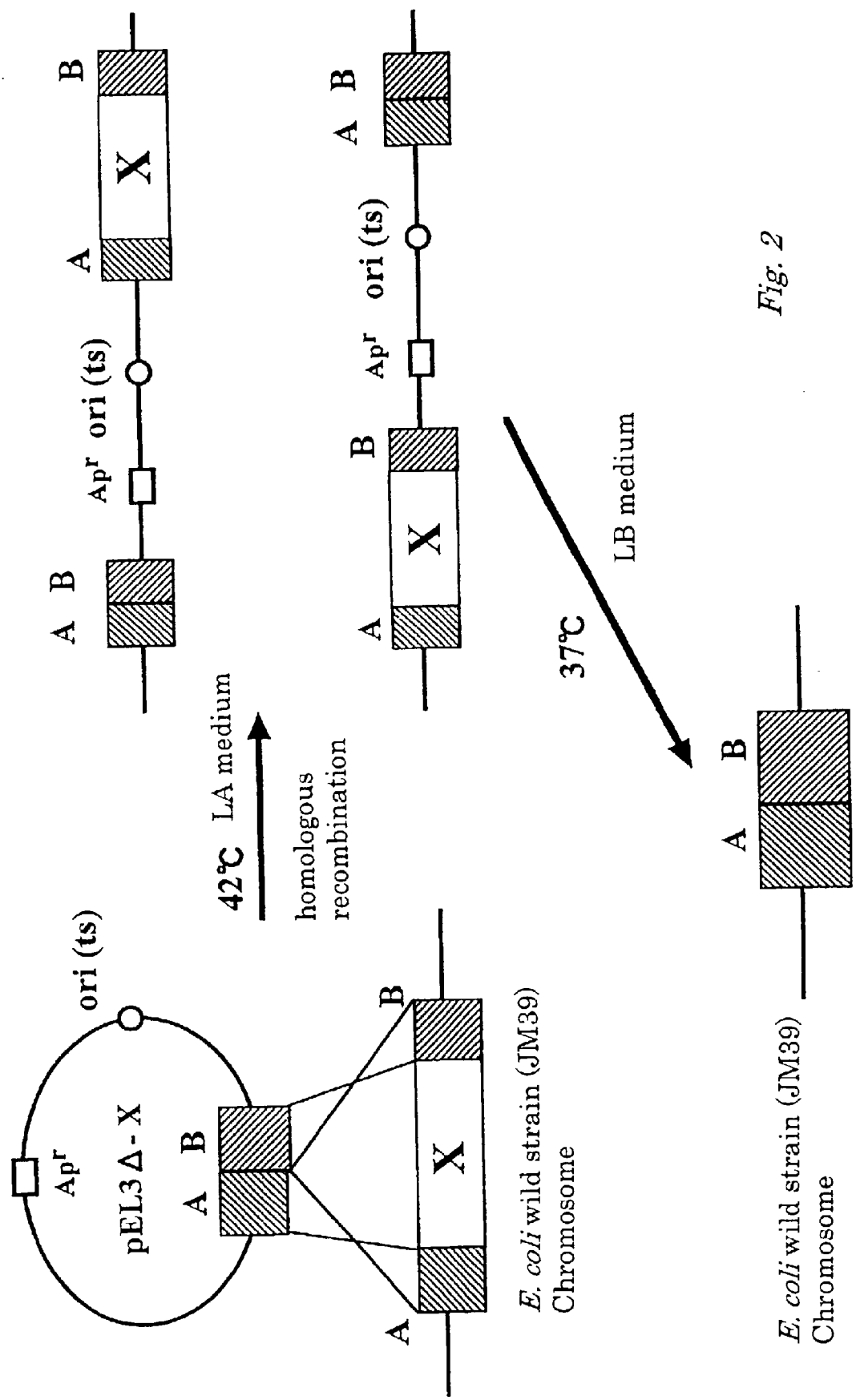
FIG. 2 shows construction scheme of metC-disrupted strain, tnaA-disrupted strain and metC/tnaA-disrupted strain of *Escherichia coli*. "A" and "B" indicate end regions of the genes, and "X" indicates a deletion region.

Because CBL and TNase were identified as enzymes having CD activity in *Escherichia coli* as described above, strains in which the gene coding for CBL, metC, or the gene coding for gene TNase, tnaA, or the both genes were disrupted were prepared in order to investigate effect of reduction of their activities on L-cysteine production (FIG. 2). The specific procedures were as follows.

(1) Construction of tnaA-Deficient Strain

PCR was performed by using chromosome DNA of the *Escherichia coli* JM109 strain as a template and each set of primers having the nucleotide sequences of SEQ ID NOS: 2 and 3 and primers having the nucleotide sequences of SEQ ID NOS: 4 and 5. Then, the PCR products were digested with HindIII and ligated. By using this reaction solution as a template and primers having the nucleotide sequences of SEQ ID NOS: 2 and 5, PCR was performed to obtain a fragment of about 1.6 kb. This fragment was digested with BamHI, incorporated into the BamHI site of a temperature sensitive plasmid pEL3 (K. A. Armstrong et al., J. Mol. Biol., 175, 331–347 (1984)) to construct a plasmid pEL3ΔtnaA for tnaA disruption.

The JM39 strain was transformed with the plasmid pEL3ΔtnaA to obtain a clone that showed ampicillin resistance at 30° C. A culture broth of this clone was appropriately diluted, plated on LB agar medium added with ampicillin and cultured overnight at 42° C. to obtain a strain corresponding to JM39 strain in which pEL3ΔtnaA was incorporated into the chromosome. Subsequently, this strain was subcultured at 37° C. on LB medium not added with ampicillin, and ampicillin-sensitive clones were separated. Regions of the chromosome around tnaA gene of the separated clones was analyzed by genomic PCR to select a strain not having the wild-type tnaA gene but having only the disrupted type tnaA cloned on pEL3ΔtnaA. Thus, a tnaA gene-disrupted strain derived from the JM39 strain, JM39ΔtnaA, was obtained.

(2) Construction of metC-Deficient Strain

PCR was performed by using chromosome DNA of the *Escherichia coli* JM109 strain as a template and each set of primers having the nucleotide sequences of SEQ ID NOS: 6 and 7 and primers having the nucleotide sequences of SEQ ID NOS: 8 and 9. Then, the PCR products were digested with by KpnI and ligated. By using this reaction solution as a template and primers having the nucleotide sequences of SEQ ID NOS: 6 and 9, PCR was performed to obtain a fragment of about 1.4 kb. This fragment was digested with BamHI, incorporated into the BamHI site of pEL3 to construct a plasmid pEL3ΔmetC for metC disruption.

The JM39 strain and the JM39ΔtnaA strain were each transformed with the plasmid pEL3ΔmetC to obtain clones that showed ampicillin resistance at 30° C. Culture broth of each clone was appropriately diluted, plated on LB agar medium added with ampicillin and cultured overnight at 42° C. to obtain a strain in which pEL3ΔmetC was incorporated into the JM39 chromosome. Subsequently, each strain was subcultured at 37° C. on LB medium not added with ampicillin, and ampicillin-sensitive clones were separated. Regions of the chromosome around metC gene of the separated clones was analyzed by genomic PCR to select a strain not having the wild-type metC gene but having only the disrupted type metC cloned on pEL3ΔmetC. Thus, a metC gene-disrupted strain derived from the JM39 strain, JM39ΔmetC, and a metC gene-disrupted strain derived from the JM39ΔtnaA strain, JM39ΔtnaAΔmetC, were obtained.

(3) Confirmation of Gene Disruption

Figure 3:
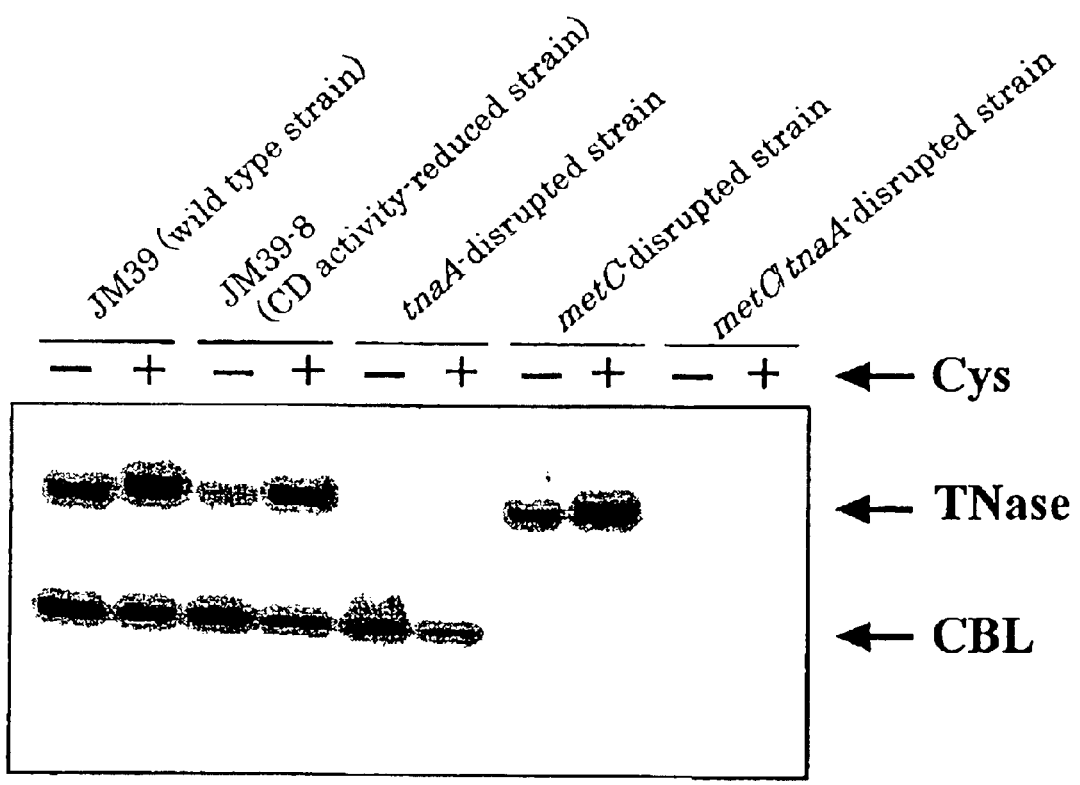
FIG. 3 shows photographs representing the results of electrophoresis and CD activity staining for confirming gene disruption of metC-disrupted strain, tnaA-disrupted strain and metC/tnaA-disrupted strain.

Then, presence or absence of a band showing the CD activity was investigated for the JM39ΔtnaA strain and the JM39ΔmetC strain by electrophoresis and activity staining (FIG. 3). As a result, the band of the larger molecular weight disappeared in the tnaA-disrupted strain, the band of the smaller molecular weight disappeared in the metC-disrupted strain, and the both bands completely disappeared in the tnaA and metC both disrupted strain.

<3>Introduction of a Gene Encoding SAT Which is Insensitive to Feedback Inhibition A gene encoding SAT which is insensitive to feedback inhibition derived from *Arabidopsis thaliana* was introduced into each of the gene-disrupted strains obtained above.

The plasmid pEAS-m containing SAT gene derived from *Arabidopsis thaliana* (FEMS Microbiol. Lett., 179, 453–459 (1999)) was used. The plasmid pES-m was obtained by using the plasmid pCE, which was used for introduction of *E. coli*-derived cysE gene as described in Japanese Patent Laid-open Publication No. 11-155571, as a base material and inserting the feedback inhibition insensitive SAT gene derived from *Arabidopsis thaliana* into the plasmid instead of the *E. coli*-derived cysE gene. The plasmid pES-m can be constructed as follows. First, the plasmid pCE is introduced with NcoI sites immediately before and after the initiation codon of the cysE gene to obtain a plasmid pCE (NcoI), according to the method described in FEMS Microbiol. Lett., 179, 453–459 (1999). This plasmid is digested with NcoI to remove the cysE gene, and the SAT gene of *Arabidopsis thaliana* added with NcoI linkers is inserted instead. The structure of the SAT gene of *Arabidopsis thaliana* is already known (Plant Molecular Biology, 30, 1041–1049 (1996)), and it can be obtained by chemical synthesis or PCR. pEAS-m was obtained by introducing, into the NcoI site of pCE, a DNA fragment obtained by inserting NcoI sites before and after the sequence of 189th to 1201st nucleotides in the nucleotide sequence described in Plant Molecular Biology, 30, 1041–1049 (1996), FIG. 2.

Figure 4:
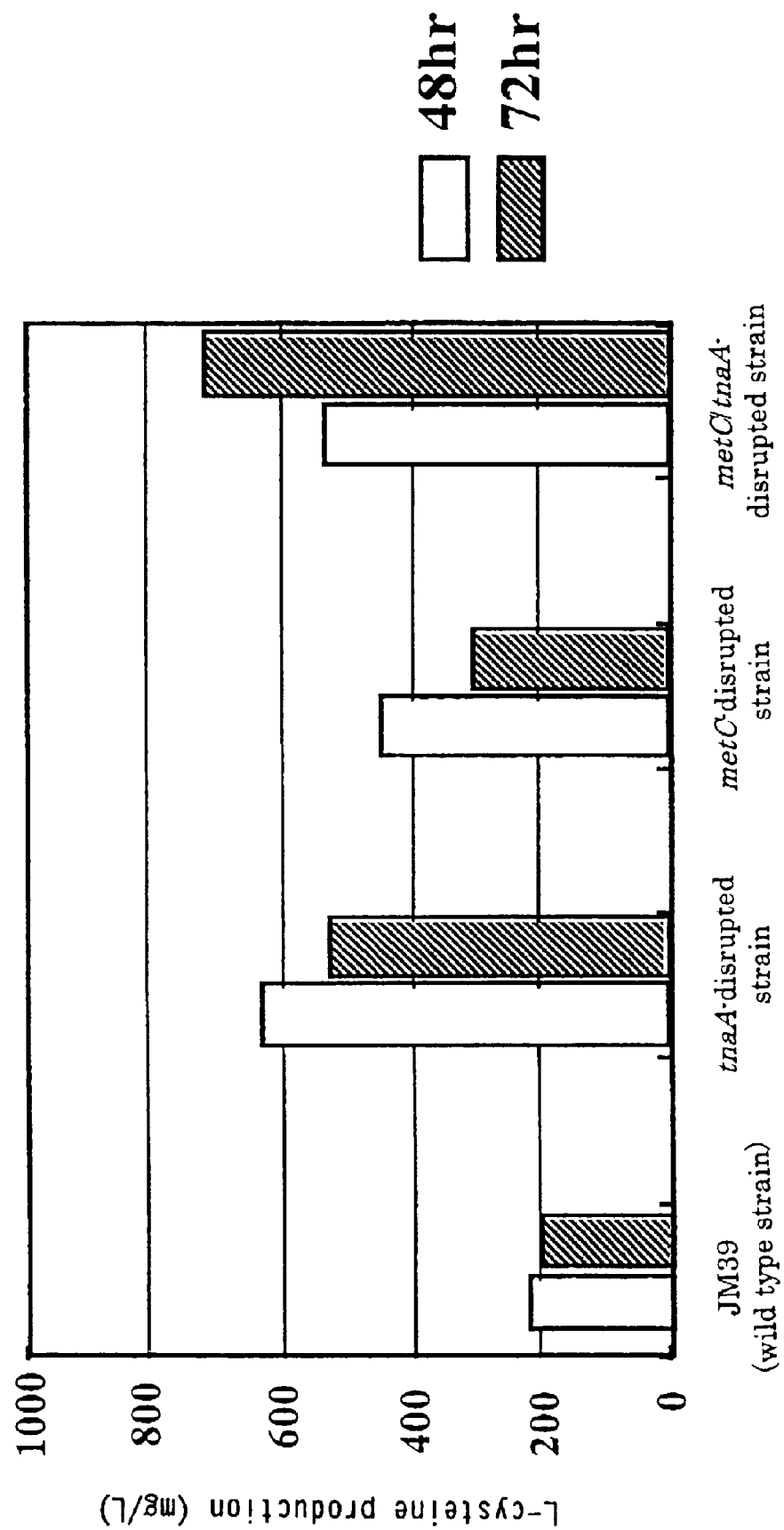
FIG. 4 shows L-cysteine productivity of metC-disrupted strain, tnaA-disrupted strain and metC/tnaA-disrupted strain.

JM39, JM39ΔtnaA, JM39ΔmetC and JM39ΔtnaAΔmetC were transformed with the aforementioned plasmid pEAS-m. Each obtained transformant was cultured at 30° C. for 24 hours on a LB plate medium containing 50 mg/L of ampicillin, and then one platinum loop of the cells were inoculated into 20 ml of C1 medium (30 g/L of glucose, 10 g/L of $NH_4Cl$, 2 g/L of $KH_2PO_4$, 1 g/L of $MgSO_4.7H_2O$, 10 mg/L of $FeSO_4.7H_2O$, 10 mg/L of $MnCl_2.4H_2O$ and 20 g/L of $CaCO_3$) added with 50 mg/L of ampicillin, which was contained in a Sakaguchi flask, and cultured at 30° C. for 48 hours or 72 hours. When L-cysteine content of the supernatant was determined by a bioassay after the culture, the content exceeded that obtained with a wild-type strain for all the disrupted strains. Thus, it was confirmed that the disruptions of tnaA and metC were effective on enhancement of L-cysteine productivity (FIG. 4).

What is claimed is:

1. A recombinant bacterium belonging to the genus *Escherichia* having an L-cysteine producing ability and modified so that an activity of endogenous cystathionine-β-lyase is reduced as compared to an unmodified bacterium belonging to the genus *Escherichia* or eliminated by modification of a polynucleotide encoding said cystathionine-β-lyase, wherein the cystathionine-β-lyase has the amino acid sequence of SEQ ID NO:11, or the cystathionine-β-lyase is encoded by a DNA selected from the group consisting of:

(a) a DNA having the nucleotide sequence of SEQ ID NO:10, and (b) a DNA which hybridizes under stringent condition with a DNA having the nucleotide sequence of SEQ ID NO:10, wherein the stringent condition comprises washing in 1×SSC, 0.1% SDS at 60° C.

2. The bacterium according to claim 1, wherein the polynucleotide encoding the cystathionine-β-lyase is disrupted.

3. The bacterium according to claim 1, further comprising modification such that the activity of the endogenous tryptophanase is reduced as compared to an unmodified bacterium belonging to the genus *Escherichia* or eliminated by modification of a polynucleotide encoding said tryptophanase, wherein the tryptophanase has the amino acid sequence of SEQ ID NO:13, or the tryptophanase is encoded by a DNA selected from the group consisting of:

(a) a DNA having the nucleotide sequence of SEQ ID NO:12, and (b) a DNA which hybridizes under stringent condition with a DNA having the nucleotide sequence of SEQ ID NO:12, wherein the stringent condition comprises washing in 1×SSC, 0.1% SDS at 60° C.

4. The bacterium according to claim 3, wherein the polynucleotide encoding the tryptophanase is disrupted.

5. The bacterium according to claim 1, further comprising modification such that the activity of the endogenous serine acetyltransferase is enhanced as compared to an unmodified bacterium belonging to the genus *Escherichia* by overexpression of a polynucleotide encoding said serine acetyltransferase, wherein the serine acetyltransferase has the amino acid sequence of SEQ ID NO:15, or the serine acetyltransferase is encoded by a DNA selected from the group consisting of:

(a) a DNA having the nucleotide sequence of SEQ ID NO:14, and (b) a DNA which hybridizes in stringent condition with a DNA having the nucleotide sequence of SEQ ID NO:14, wherein the stringent condition comprises washing in 1×SSC, 0.1% SDS at 60° C.

6. The bacterium according to claim 3, further comprising modification such that the activity of the endogenous seine acetyltransferase is enhanced as compared to an unmodified bacterium belonging to the genus *Escherichia* by overexpression of a polynucleotide encoding said serine acetyltransferase, wherein the modified serine acetyltransferase has the amino acid sequence of SEQ ID NO:15 or the serine acetyltransferase is encoded by a DNA selected from the group consisting of:

(a) a DNA having the nucleotide sequence of SEQ ID NO:14, and (b) a DNA which hybridizes under stringent condition with a DNA having the nucleotide sequence of SEQ ID NO:14, wherein the stringent condition comprises washing in 1×SSC, 0.1% SDS at 60° C.

7. The bacterium according to claim 1, wherein said bacterium is *Escherichia coli*.

8. A method for producing L-cysteine, comprising culturing the bacterium according to claim 7 in a medium to produce and accumulate L-cysteine in the medium and collecting the L-cysteine from the medium.

9. The bacterium according to claim 3, wherein said bacterium is *Escherichia coli*.

10. A method for producing L-cysteine, comprising culturing the bacterium according to claim 9 in a medium to produce and accumulate L-cysteine in the medium and collecting the L-cysteine from the medium.

11. The bacterium according to claim 5, wherein said bacterium is *Escherichia coli*.

12. A method for producing L-cysteine, comprising culturing the bacterium according to claim 11 in a medium to produce and accumulate L-cysteine in the medium and collecting the L-cysteine from the medium.

13. The bacterium according to claim 6, wherein said bacterium is *Escherichia coli*.

14. A method for producing L-cysteine, comprising culturing the bacterium according to claim 13 in a medium to produce and accumulate L-cysteine in the medium and collecting the L-cysteine from the medium.

15. A method for producing L-cysteine, comprising culturing the bacterium according to claim 1 in a medium to produce and accumulate L-cysteine in the medium and collecting the L-cysteine from the medium.

16. A method for producing L-cysteine, comprising culturing the bacterium according to claim 3 in a medium to produce and accumulate L-cysteine in the medium and collecting the L-cysteine from the medium.

17. A method for producing L-cysteine, comprising culturing the bacterium according to claim 5 in a medium to produce and accumulate L-cysteine in the medium and collecting the L-cysteine from the medium.

18. A method for producing L-cysteine, comprising culturing the bacterium according to claim 6 in a medium to produce and accumulate L-cysteine in the medium and collecting the L-cysteine from the medium.

* * * * *